US008721612B2

(12) United States Patent
Domkowski et al.

(10) Patent No.: US 8,721,612 B2
(45) Date of Patent: May 13, 2014

(54) SYSTEM AND METHOD FOR INTERMIXING THE CONTENTS OF TWO CONTAINERS

(75) Inventors: John Domkowski, Kenosha, WI (US); Eric Schmidt, Forest Park, IL (US)

(73) Assignee: Hospira, Inc., Lake Forest, IL (US)

( * ) Notice: Subject to any disclaimer, the term of this patent is extended or adjusted under 35 U.S.C. 154(b) by 23 days.

(21) Appl. No.: 13/328,983

(22) Filed: Dec. 16, 2011

(65) Prior Publication Data

US 2012/0330267 A1 Dec. 27, 2012

Related U.S. Application Data

(60) Provisional application No. 61/424,263, filed on Dec. 17, 2010.

(51) Int. Cl.
*A61B 19/00* (2006.01)
*A61J 1/20* (2006.01)

(52) U.S. Cl.
CPC . *A61J 1/2089* (2013.01); *A61J 1/20* (2013.01)
USPC .......................................... 604/408; 604/403

(58) Field of Classification Search
CPC ......... A61J 1/2089; A61J 1/2096; A61J 1/10; A61J 1/12; A61J 1/1406; A61J 1/1412
USPC ................................................ 604/403–416
See application file for complete search history.

(56) References Cited

U.S. PATENT DOCUMENTS

| | | | |
|---|---|---|---|
| 2,176,923 | A | 10/1939 | Nitardy |
| 2,372,181 | A | 3/1945 | Barr |
| 3,290,017 | A | 12/1966 | Davies et al. |
| 3,464,414 | A | 9/1969 | Sponnoble |
| 3,532,254 | A | 10/1970 | Burke et al. |
| 3,857,392 | A | 12/1974 | Ogle |
| 3,872,992 | A | 3/1975 | Larson |
| 4,089,432 | A | 5/1978 | Crankshaw et al. |
| 4,102,451 | A | 7/1978 | Clarke et al. |
| 4,123,091 | A | 10/1978 | Cosentino et al. |
| 4,185,747 | A | 1/1980 | Goncalves |
| 4,194,640 | A | 3/1980 | Crankshaw et al. |
| 4,226,334 | A | 10/1980 | Weiler et al. |

(Continued)

FOREIGN PATENT DOCUMENTS

| | | |
|---|---|---|
| DE | 297 21 872 | 3/1998 |
| EP | 0 335 378 | 10/1989 |

(Continued)

OTHER PUBLICATIONS

Extended European Search Report for EP10160160.7 including concise summary of DE 297 21 872 (Oct. 6, 2010).

(Continued)

*Primary Examiner* — Philip R Wiest
*Assistant Examiner* — Benjamin Klein
(74) *Attorney, Agent, or Firm* — Brian R. Woodworth

(57) ABSTRACT

A system and method for intermixing the contents of two containers. The system includes a first container, a second container, and a connector for providing fluid communication between the first and second containers. The connector includes at least one resilient retention member for securing the first container to the connector. In addition, the connector accommodates standard vials containing, for example, medicaments, and prevents the unwanted discharge of the contents of the vial into the environment.

17 Claims, 11 Drawing Sheets

(56) References Cited

U.S. PATENT DOCUMENTS

| | | | |
|---|---|---|---|
| 4,333,505 A | 6/1982 | Jones et al. | |
| 4,394,922 A | 7/1983 | Wimmer | |
| 4,444,330 A | 4/1984 | Kasai et al. | |
| 4,458,811 A | 7/1984 | Wilkinson | |
| 4,488,656 A | 12/1984 | Fukuoka et al. | |
| 4,526,572 A | 7/1985 | Donnan et al. | |
| 4,544,074 A | 10/1985 | Evans | |
| 4,610,684 A | 9/1986 | Knox et al. | |
| 4,614,267 A | 9/1986 | Larkin | |
| 4,614,515 A | 9/1986 | Tripp et al. | |
| 4,703,864 A | 11/1987 | Larkin et al. | |
| 4,757,911 A | 7/1988 | Larkin et al. | |
| 4,759,756 A * | 7/1988 | Forman et al. | 604/413 |
| 4,770,445 A | 9/1988 | Steer et al. | |
| 4,781,679 A | 11/1988 | Larkin | |
| 4,784,259 A | 11/1988 | Grabenkort | |
| 4,784,658 A | 11/1988 | Grabenkort | |
| 4,871,354 A | 10/1989 | Conn et al. | |
| 4,871,654 A | 10/1989 | Vanmaaele et al. | |
| 4,936,445 A | 6/1990 | Grabenkort | |
| 4,936,841 A | 6/1990 | Aoki et al. | |
| 4,948,000 A | 8/1990 | Grabenkort | |
| 4,963,441 A | 10/1990 | Takai et al. | |
| 4,998,671 A | 3/1991 | Lefheit | |
| 5,060,812 A | 10/1991 | Ogle, II | |
| 5,064,059 A * | 11/1991 | Ziegler et al. | 206/221 |
| 5,066,280 A | 11/1991 | Braithwaite | |
| 5,066,286 A | 11/1991 | Ryan | |
| 5,088,994 A | 2/1992 | Porat et al. | |
| 5,102,408 A | 4/1992 | Hamacher | |
| 5,139,483 A | 8/1992 | Ryan | |
| 5,176,526 A | 1/1993 | Hillbish et al. | |
| 5,195,994 A | 3/1993 | Dieringer | |
| 5,222,486 A | 6/1993 | Vaughn | |
| 5,290,222 A | 3/1994 | Feng et al. | |
| 5,292,308 A | 3/1994 | Ryan | |
| 5,332,399 A | 7/1994 | Grabenkort et al. | |
| 5,335,773 A | 8/1994 | Haber et al. | |
| 5,358,501 A | 10/1994 | Meyer | |
| 5,380,315 A | 1/1995 | Isono et al. | |
| 5,423,793 A | 6/1995 | Isono et al. | |
| 5,462,526 A | 10/1995 | Barney et al. | |
| 5,478,337 A | 12/1995 | Okamoto et al. | |
| 5,526,853 A | 6/1996 | McPhee et al. | |
| 5,527,580 A | 6/1996 | Ikeda et al. | |
| 5,545,152 A | 8/1996 | Funderburk et al. | |
| 5,620,427 A | 4/1997 | Werschmidt et al. | |
| 5,785,701 A | 7/1998 | Sams et al. | |
| 5,855,568 A | 1/1999 | Battiato et al. | |
| 5,928,213 A | 7/1999 | Barney et al. | |
| 5,944,709 A | 8/1999 | Barney et al. | |
| 5,947,954 A | 9/1999 | Bonaldo | |
| 5,989,237 A | 11/1999 | Fowles et al. | |
| 6,004,297 A | 12/1999 | Steenfeldt-Jensen et al. | |
| 6,063,068 A | 5/2000 | Fowles et al. | |
| 6,071,270 A | 6/2000 | Fowles et al. | |
| 6,096,024 A | 8/2000 | Graves et al. | |
| 6,113,583 A | 9/2000 | Fowles et al. | |
| 6,159,192 A | 12/2000 | Fowles et al. | |
| 6,203,535 B1 | 3/2001 | Barney et al. | |
| 6,258,078 B1 | 7/2001 | Thilly | |
| 6,382,442 B1 * | 5/2002 | Thibault et al. | 215/249 |
| 6,413,242 B1 | 7/2002 | Michel et al. | |
| 6,610,040 B1 | 8/2003 | Fowles et al. | |
| 6,729,370 B2 | 5/2004 | Norton et al. | |
| 6,846,305 B2 | 1/2005 | Smith et al. | |
| 6,874,522 B2 | 4/2005 | Anderson et al. | |
| 6,910,573 B2 | 6/2005 | Deans | |
| 6,913,595 B2 | 7/2005 | Mastoraskis | |
| 6,962,321 B1 | 11/2005 | Savage et al. | |
| 7,115,117 B2 | 10/2006 | Shiraishi et al. | |
| 7,316,679 B2 | 1/2008 | Bierman | |
| 7,347,458 B2 | 3/2008 | Rome et al. | |
| 7,473,246 B2 | 1/2009 | Vancaillie et al. | |
| 7,497,484 B2 | 3/2009 | Ziman | |
| 7,540,863 B2 | 6/2009 | Haindl | |
| 7,544,191 B2 | 6/2009 | Peluso et al. | |
| 7,600,515 B2 | 10/2009 | Matlock | |
| 7,615,041 B2 | 11/2009 | Sullivan et al. | |
| 7,862,539 B2 | 1/2011 | Knight | |
| 7,938,815 B2 | 5/2011 | Shoji et al. | |
| 7,998,134 B2 | 8/2011 | Fangrow et al. | |
| 8,075,545 B2 | 12/2011 | Moy et al. | |
| 8,162,013 B2 | 4/2012 | Rosenquist et al. | |
| 8,216,207 B2 | 7/2012 | Moy et al. | |
| 8,221,382 B2 | 7/2012 | Moy et al. | |
| 8,241,265 B2 | 8/2012 | Moy et al. | |
| 2003/0106610 A1 | 6/2003 | Roos et al. | |
| 2003/0187420 A1 | 10/2003 | Akerlund et al. | |
| 2003/0201641 A1 | 10/2003 | Guest | |
| 2004/0186457 A1 | 9/2004 | Truitt et al. | |
| 2004/0201216 A1 | 10/2004 | Segal et al. | |
| 2005/0015075 A1 | 1/2005 | Wright et al. | |
| 2005/0045669 A1 | 3/2005 | Thunberg et al. | |
| 2005/0055008 A1 | 3/2005 | Paradis et al. | |
| 2006/0030832 A1 * | 2/2006 | Niedospial et al. | 604/411 |
| 2006/0282061 A1 | 12/2006 | Domkowski et al. | |
| 2007/0088315 A1 | 4/2007 | Haindl | |
| 2007/0102393 A1 | 5/2007 | Colin et al. | |
| 2009/0032489 A1 | 2/2009 | Moy et al. | |
| 2009/0036861 A1 | 2/2009 | Moy et al. | |
| 2009/0036864 A1 | 2/2009 | Moy et al. | |
| 2009/0036865 A1 | 2/2009 | Moy et al. | |
| 2009/0036866 A1 | 2/2009 | Moy et al. | |
| 2009/0069783 A1 | 3/2009 | Ellstrom et al. | |
| 2009/0259197 A1 | 10/2009 | Christiansen | |
| 2009/0270832 A1 | 10/2009 | Vancaillie et al. | |
| 2010/0148500 A1 | 6/2010 | Uehara et al. | |
| 2010/0152669 A1 | 6/2010 | Rosenquist | |
| 2010/0211019 A1 | 8/2010 | Greco | |
| 2010/0241088 A1 | 9/2010 | Ranalletta et al. | |
| 2011/0015580 A1 | 1/2011 | Stroup et al. | |
| 2011/0125128 A1 | 5/2011 | Nord et al. | |
| 2011/0137294 A1 | 6/2011 | Calimeri et al. | |
| 2011/0193004 A1 | 8/2011 | Lahaye | |
| 2012/0136317 A1 | 5/2012 | Teucher et al. | |
| 2012/0330267 A1 | 12/2012 | Domkowski et al. | |

FOREIGN PATENT DOCUMENTS

| | | |
|---|---|---|
| EP | 0 633 038 | 1/1995 |
| EP | 0 503 867 | 2/1997 |
| FR | 2931363 | 11/2009 |
| FR | 2952873 | 5/2011 |
| GB | 1419061 | 12/1975 |
| JP | 8243171 | 9/1996 |
| JP | 10024088 | 1/1998 |
| JP | 2002017871 | 1/2002 |
| JP | 2003200977 | 7/2003 |
| JP | 2007236567 | 9/2007 |
| JP | 2007295998 | 11/2007 |
| WO | 98/14163 | 4/1998 |
| WO | 98/44257 | 10/1998 |
| WO | 01/023026 | 4/2001 |
| WO | 2008/115102 | 9/2008 |
| WO | 2009/024807 | 2/2009 |
| WO | 2009/035383 | 3/2009 |
| WO | 2000/066921 | 11/2009 |
| WO | 2010/069361 | 6/2010 |

OTHER PUBLICATIONS

"Special 510(k) Premarket Notification—addEASE 20mm Binary Connector with 17 Ga. Needle," B. Braun Medical, Inc., Mar. 27, 2009. Describing the B. Braun addEASE Connector.
"addEASE Binary Connector with 17 Ga. Needle," B. Braun Medical Inc., 2011. Describing the B. Braun addEASE Connector.
"B. Braun addEASE Binary Connector," Medical Device Recalls, U.S. Food and Drug Administration, Jun. 24, 2010. Describing the B. Braun addEASE Connector.

* cited by examiner

SECTION A - A

SECTION C - C

SECTION E - E

SECTION F - F

SYSTEM AND METHOD FOR INTERMIXING THE CONTENTS OF TWO CONTAINERS

CROSS-REFERENCE TO RELATED APPLICATIONS

This application claims the benefit of U.S. Provisional Patent Application No. 61/424,263, filed on Dec. 17, 2010, and titled "System and Method for Intermixing the Contents of Two Containers."

FIELD OF THE INVENTION

This invention relates to a system and method for intermixing the contents of two separate containers that avoids discharge of the contents of the containers into the environment while maintaining sterility of the system.

BACKGROUND OF THE INVENTION

Many compounds for medical use are packaged separately from diluents used to facilitate administration of the compound to a patient. These medical compounds are packaged in a variety of known pharmaceutical containers (e.g., vials) in solid (e.g., lyophilized or spray-dried) form, in liquid form, in other forms. Prior to administration of these compounds to a patient, the compounds are mixed with a variety of known diluents in order to reconstitute, dilute, and/or facilitate intravenous or subcutaneous delivery to a patient. The diluents used can contain additional active compounds, if desired. In order to maintain the sterility of both the compound and the diluent in their respective containers, it is desirable to provide a system for intermixing that is substantially closed, i.e., one that does not expose the compound or diluent to the external environment. Such exposure could negatively affect the sterility of the resulting mixture of the compound and diluent, or, in the case of hazardous compounds, could expose healthcare workers to the hazardous compound.

Systems for facilitating the safe transfer and mixing of medical compounds and diluents stored in separate containers are known. For example, a system involving packaging of a medicament and a diluent in separate containers, which may be connected to one another at the time of use for convenient, safe intermixing of the medicament and diluent in a sterile environment is currently sold by Hospira, Inc. (Lake Forest, Ill.), the owner of this application, under the trademark ADD-VANTAGE. A number of details of the ADD-VANTAGE system are disclosed in U.S. Pat. Nos. 4,757,911; 4,703,864; 4,784,658; 4,784,259; 4,948,000; 4,936,445; 5,064,059; and 5,332,399, all of which are incorporated herein by reference.

In one example of the ADD-VANTAGE system referenced above, a flexible diluent container includes a receiving port constructed to receive a medicament vial closed by a vial stopper. The receiving port is positioned at the top end of the diluent container, i.e., the end of the diluent container that is on top when the diluent container is hung for delivery of its contents to a patient. The flexible diluent container further includes a stopper removal member configured to connect to the vial stopper by engaging an undercut or shouldered recess in the exposed end of the vial stopper. Securement of the vial and the diluent container is accomplished by threadable engagement of threads that circumscribe the outside of the neck portion (which defines the vial opening) of the vial with complementary threads within the diluent container port. Additionally, ratchet teeth, which circumscribe the outside of a skirt member of the vial, engage with complementary ratchet teeth located on the interior of the diluent container port. The slopes of the ratchet teeth are such that once engagement is initiated, the vial cannot be backed out of the port without causing visible damage to the vial and/or port, thereby obviating any contamination which may be occasioned by vial-container disengagement and reengagement. In other words, the ratchet teeth are "one-way" ratchet teeth. Further, as the stoppered vial is advanced into and engaged with the port of the diluent container, the vial stopper advances onto the stopper removal member. The stopper removal member is thereby secured to the stopper such that the stopper may subsequently be pulled and removed (via manipulation of the stopper removal member) from the vial, thereby allowing intermixing of the contents of the two containers.

The flow path created as a result of activating the stopper removal member of the ADD-VANTAGE system is defined by the neck of the vial and the dimension of the flow channel defined through the port of the diluent container. The dimension of this flow path is sufficient to permit the contents of the diluent container to flow readily into and out of the vial, e.g., by "sloshing" the diluent container. By providing significant flow of fluid between the vial and the diluent container, the ADD-VANTAGE system provides quick and thorough mixing. Further, because the vial is positioned at the top end of the diluent container when the contents of the diluent container are delivered to a patient, any contents remaining in the vial will flow into the diluent container.

In the ADD-VANTAGE system, securement of the vial and diluent container, and subsequent intermixing of their respective contents, requires that the vial and the container be complementary and be manufactured to specifically connect to each other.

An example of an alternative transfer system is the add-EASE binary connector sold by B. Braun Medical, Inc. A first end of the add-EASE connector includes a structure for receiving and securing the connector to a pharmaceutical vial. The first end includes a first spike for penetrating an elastomeric stopper sealing the vial. The second end of the add-EASE connector includes a structure for receiving and securing the connector to a port of a diluent container. The second end includes a second spike for penetrating an elastomeric closure associated with the port of the diluent container. Once the add-EASE connector has been secured to both the vial and the diluent container, pressure is applied to the contents of the diluent container. This pressure results in a force being applied to a plug member positioned within the first spike, thereby moving the plug from the first spike and into the vial. Because of the relatively narrow flow channel defined by the first and second spikes of the add-EASE connector, it is necessary to pump or "milk" diluent out of the diluent container and into the vial in order to reconstitute and/or dilute the drug contained in the vial. It also is necessary to pump or "milk" the resulting diluent/drug mixture out of the vial back into the diluent container for delivery to the patient. Further, because the diluent container port is positioned at the bottom of the diluent container, i.e., at the end of the diluent container that is positioned closest to the floor when the contents of the diluent container are delivered to a patient, the dimension of the flow channel defined by the first and second spikes must remain small in order to prevent contents of the diluent container from flowing back into the vial (rather than flowing to the patient).

In light of the above-described systems and their respective characteristics, the inventors have identified a need in the art for a system for intermixing substances that uses a diluent container similar to the ADD-VANTAGE diluent container described above but does not require a dedicated, complementary vial.

SUMMARY

Disclosed herein are various embodiments of a system and corresponding method that use a connector that allows a user (e.g., a pharmacist or other healthcare worker) to intermix at least two substances from two separate containers while maintaining sterility and preventing unwanted release of the substances into the environment. Various embodiments of the connector are also disclosed.

According to one embodiment of the system, the system includes a first container, a second container, and a connector for providing fluid communication between the first and second containers. The first container may be a medicament container such as a vial. The second container may be a diluent container such as an intravenous (IV) bag. In one example, the connector accommodates standard vials.

According to another embodiment of the system, the system includes (i) a first container (with a first substance) comprising a pierceable seal for sealing the distal end of the first container, (ii) a second container (with a second substance) comprising (a) a receiving port with a securing mechanism and (b) a removable sealing member for sealing the receiving port, and (iii) a connector for connecting the first and second containers. The connector includes (a) a body having a proximal end with a cavity for engaging the first container and a distal end with an opening and a securing mechanism that is complementary to the securing mechanism of the second container, (b) a penetrating member with a flow passageway for providing fluid communication between the containers, and (c) at least one resilient retention member within the cavity for securing the distal end of the first container. The penetrating member extends in the proximal direction from a position within the cavity, and is configured to pierce the seal of the first container.

In another embodiment, the removable sealing member of the second container prevents the first and second substances from intermixing until the removable sealing member is disengaged from the receiving port of the second container. The first and second substances may be intermixed by inverting or shaking the system after (i) the first and second containers are secured to the connector and (ii) the removable sealing member is disengaged from the receiving port of the second container.

In another embodiment, the connector also includes a removable plug located near the distal end of the connector. The removable plug seals the opening of the connector and is configured to engage the removable sealing member of the second container when the second container is connected to the connector. The removable plug may also include a recess with an undercut for engaging the removable sealing member of the second container such that the removable plug may be removed from the connector by removing the removable sealing member from the receiving port. The removable sealing member of the second container and the removable plug of the connector may prevent the first and second substances from intermixing until the removable sealing member is disengaged from the receiving port of the second container and the removable plug is disengaged from the opening of the connector.

In another embodiment, the receiving port of the connector includes complementary ratchet teeth that prevent the connector from being removed from the receiving port when the securing mechanism of the connector is engaged with securing mechanism of the second container.

In another embodiment, the at least one resilient retention member of the connector is configured to engage a shoulder of the first container and inhibit removal of the first container from the connector after a distal end of the first container is inserted a predetermined distance into the cavity. The resilient retention member may extend distally inwardly within the cavity. In one example, the connector includes at least two resilient retention fingers.

In another embodiment, the at least one resilient retention member is attached to the body of the connector via at least two tabs. After the first container is docked to the connector, removal of the first container may cause at least one of the at least two tabs to break, thereby providing a visual indication that the first container was removed and discouraging reuse of the connector.

In another embodiment, fluid communication between the first and second containers is established by externally manipulating the second container such that the removable sealing member is removed from the receiving port of the second container.

According to one embodiment of the connector, the connector comprises (i) a body including a proximal end with a cavity for engaging the first container and a distal end having an opening, (ii) a penetrating member extending in the proximal direction from a position within cavity, where a proximal end of the penetrating member is configured to pierce a seal of the first container and includes an aperture and a flow passageway that provides fluid communication from the aperture to the opening of the distal end, (iii) at least one resilient retention member for securing the first container to the connector, where the at least one resilient retention finger is positioned (a) within the cavity near the proximal end of the body and (b) laterally offset from the penetrating member, and where the at least one resilient retention member is configured to engage a shoulder of the first container, and prevent removal of the first container from the connector after a distal end of the first container is inserted a predetermined distance into the cavity, and (iv) two securing mechanisms for securing the connector to the second container. One of the securing mechanisms comprises threads circumscribing the exterior of the opening and the other securing mechanism comprises ratchet teeth configured to allow engagement but not disengagement of threads on a complementary securing mechanism of the second container.

In another embodiment, the connector does not prevent fluid communication between the first and second containers.

According to another embodiment of the connector, the connector comprises (i) a body including a proximal end with a cavity for receiving and engaging the first container and a distal end having an opening for providing fluid communication with the second container, (ii) at least one resilient retention member for securing the first container to the connector, where the at least one resilient retention finger is positioned within the cavity near the proximal end of the body and is attached to the body via at least two tabs forming a slit therebetween. The at least one resilient retention member is configured to engage a shoulder of the first container, and inhibit removal of the first container from the connector after a distal end of the first container is inserted a predetermined distance into the cavity.

In another embodiment, the at least two tabs attaching the at least one resilient retention finger to the body of the connector have a thickness less than that of the at least one retention member. In such an embodiment, removal of the first container from the connector may cause at least one of the at least two tabs to break. In another example, the force required to engage the first container and the connector is between 10-20 lbf.

According to one embodiment of the method, the method comprises (i) providing a system in accordance with one of the above-described embodiments, (ii) connecting the first and second containers to the connector, (iii) removing the removable sealing member by externally manipulating the second container, and (iv) intermixing the first and second substances.

In another embodiment, the second container may be connected to the connector before the first container is connected to the connector. However, in another example the first container may be connected to the connector before the second container is connected to the connector.

And it is expressly contemplated that any alternative, permutation, or other variation or feature of any disclosed embodiment may apply to any other embodiment, to the extent that alternative, permutation, or other variation or feature would be consistent and compatible with such other embodiment. In other words, disclosure of a given alternative, permutation, or other variation or feature of the system, connector, method, and/or any other component or step, or collection of components and steps in connection with a given embodiment thereof is in no way intended to be limited to that given embodiment. Furthermore, it should be noted that the above overview is intended to be illustrative and not limiting.

DETAILED DESCRIPTION

The system and corresponding method disclosed herein allow a user (e.g., a pharmacist or other healthcare worker) to intermix at least two substances from two separate containers while maintaining sterility and preventing unwanted release of the substances into the environment.

The type, size, shape, and material of the containers are not critical features of the invention. Nor are the containers' contents. The invention is appropriate for all types and sizes of containers, and for all type of contents. As described more fully below, the containers should have features that allow for sealing engagement between the connector and the containers to provide an airtight and sterile fluid communication between the containers.

A. Structure

Figure 1:
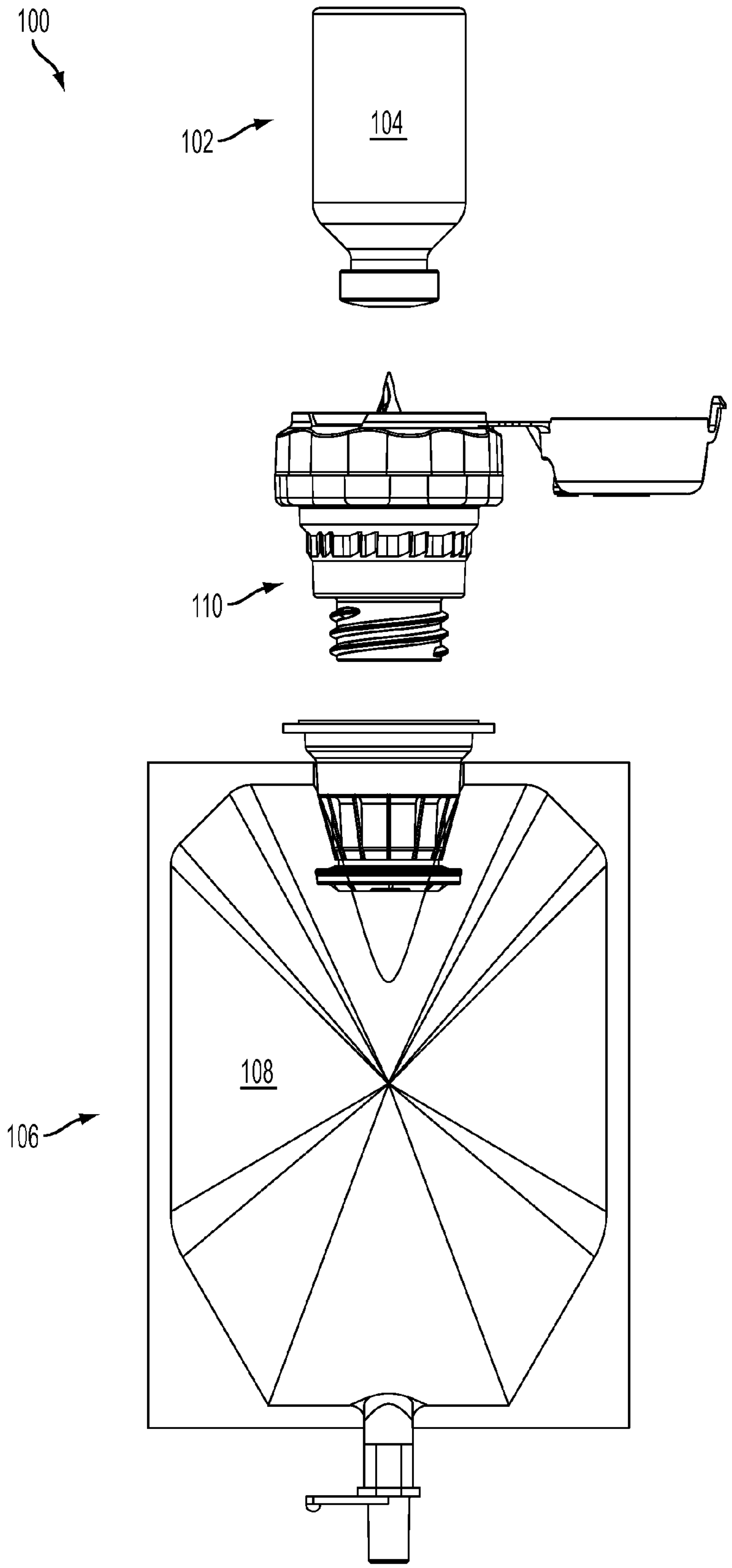
FIG. 1 illustrates an exploded view of an example system for intermixing at least two substances.

FIG. 1 illustrates an exploded view of one example of the system. As shown, the exemplary system 100 includes a first container 102 (e.g., a standard pharmaceutical vial) that contains a first substance 104, a second container 106 (e.g., an intravenous (IV) bag or other diluent container) that contains a second substance 108, and a connector 110 for connecting the first and second containers.

Figures 2A, 2B, 3A, 3B:
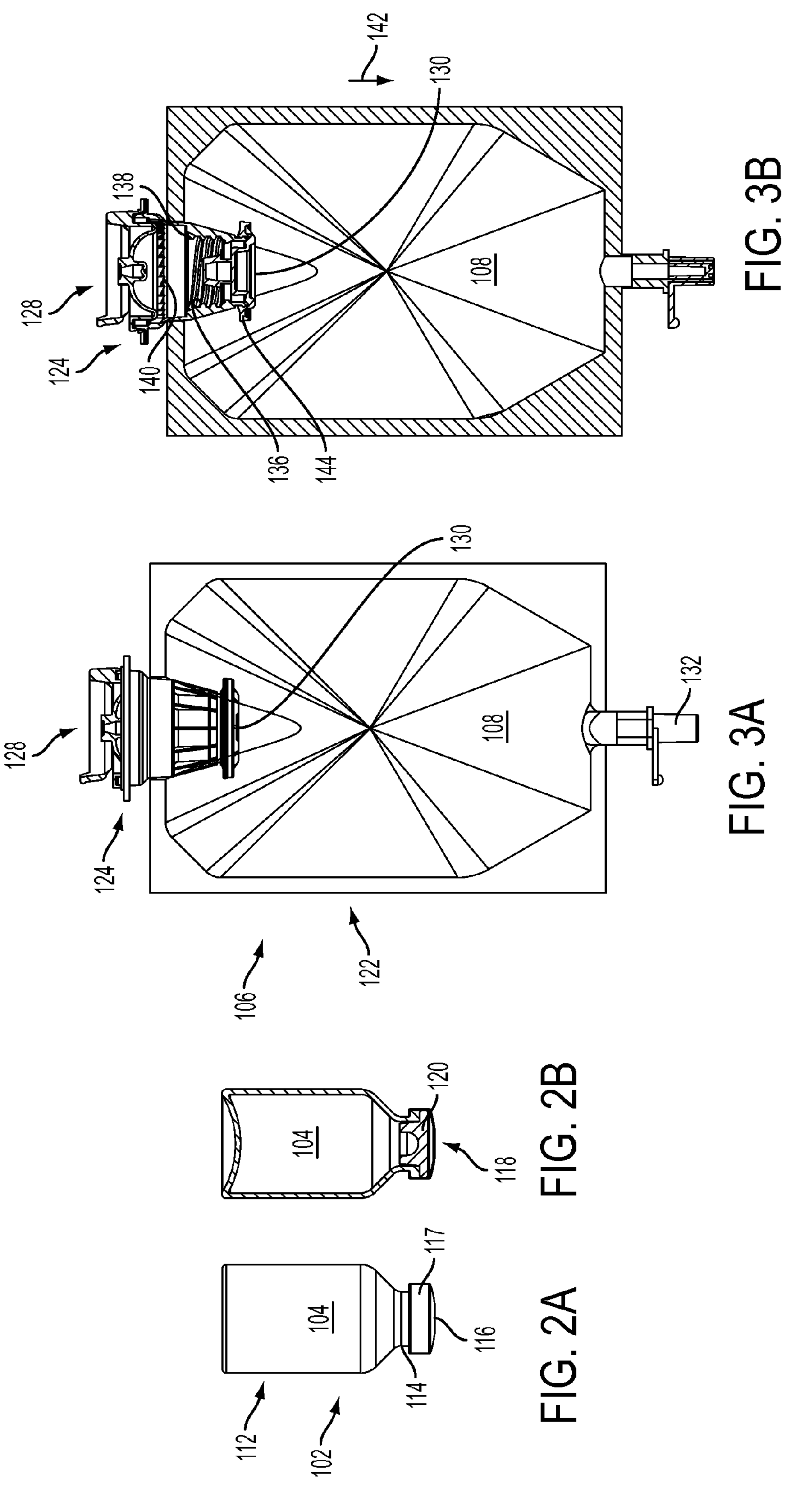
FIG. 2*a* illustrates an example first container that can be used with the system shown in FIG. 1.
FIG. 2*b* illustrates a cross-sectional view of the first container shown in FIG. 2*a*.
FIG. 3*a* illustrates an example second container that can be used with the system shown in FIG. 1.
FIG. 3*b* illustrates a cross-sectional view of the second container shown in FIG. 3*a*.

An exemplary embodiment of the first container 102 shown in FIG. 1 is illustrated in FIGS. 2*a* and 2*b*. In this embodiment, first container 102 is a standard medicament-containing vial known in the art having a generally cylindrical body 112 and a neck portion 114 near its distal end 116 that defines the container opening 118. Although shown and described herein as having a generally cylindrical body 112, the first container 102 may have a different body geometry.

The neck portion 114 includes a shoulder 117 that circumscribes the container opening 118. A resilient, pierceable seal 120 (e.g., a pharmaceutical vial stopper) prevents discharge of the first substance 104 from the container. Other examples of the first container 102 may include a different type of seal, such as a septum. The first substance 104 may be any liquid or solid substance, and generally includes medicaments that are intended to be dissolved or diluted before delivery to a patient, for example, through intravenous or subcutaneous delivery.

Many medicaments for intravenous delivery are provided in a dried form (e.g., lyophilized or spray-dried) in a standard vial. When the connector 110 is used to connect the vial 102 to a diluent container 106, fluid communication can be established between the vial and the diluent container. Diluent can enter the vial and dissolve the dried contents, which can then be transferred to the diluent container prior to administration to the patient.

FIGS. 3*a* and 3*b* illustrate an exemplary embodiment of the second container 106 of the system 100 shown in FIG. 1. As shown, the second container 106 is a flexible IV container that includes a body 122 made of a flexible material known in the art (e.g., a container constructed of PVC or a container constructed of a PVC- and DEHP-free material such as the VISIV® container marketed by Hospira, Inc.), an outlet 132, and a receiving port 124 defined in part by an opening 128 and an inner surface 138 that are configured to engage the connector 110. The inner surface 138 includes at least one mechanism for securing the connector 110 to the receiving port 124. In the depicted example, the inner surface includes two securing mechanisms, threads 136 and one-way ratchet teeth 140, both of which circumscribe the opening 128. Herein, the threads 136 and ratchet teeth 140 are collectively referred to as "securing mechanisms" of the second container 106. These securing mechanisms 136, 140 enable the second container 106 to be unreleasably secured to the connector 110. Of course, with a sufficient amount of force, the second container 106 can be separated from the connector 110 but not without visibly damaging the connector and/or second container.

Although in this example both securing mechanisms 136, 140 completely circumscribe the opening 128, in other examples, one or both of the securing mechanisms may only partially circumscribe the opening. Moreover, the securing mechanisms 136, 140 can have alternative configurations. For example, it is possible to incorporate ratchet teeth 140 into the form of threads 136 so as to provide both functionalities in a single structure. Alternative securing mechanisms that allow the vial 102 to be secured to receiving port 124 of second container 106 in a manner that substantially prevents subsequent detachment of the vial 102 are possible using known techniques and structures.

When the second container 106 is secured to the connector 110, the threads 136 in the receiving port 124 of the second container 106 engage complementary threads 177 on the connector 110 as described below, and the ratchet teeth 140 allow the threaded engagement, but not the disengagement of the threads 136, 177. In addition to threads and ratchet teeth, other types of securing mechanisms may be used for ensuring that the connector 110, once engaged with the second container 106, cannot be removed. This allows for a permanent and sterile communication between the connector 110 and the second container 106, and prevents accidental discharge of the contents 108 of the second container 106 (and the contents 104 of the first container 102, once connected) into the environment, for example, due to an operator accidentally unscrewing the connector 110 from the second container 106.

The receiving port 124 also includes a removable sealing member 130 positioned partially within the receiving port 124 and partially within an interior chamber defined by body 122. When the removable sealing member 130 is engaged (e.g., by a press or snap fit) with the receiving port 124, as depicted in FIGS. 3*a* and 3*b*, the removable sealing member provides a fluid-tight seal that prevents the second substance 108 from leaking out of the receiving port 124 while simultaneously preventing the flow of fluids through receiving port 124 into body 122. The removable sealing member 130 can be disengaged from the receiving port 124 by pulling or pushing down (in the distal direction 142) on the flange 144 of the removable sealing member. This can be accomplished by manually engaging removable sealing member 130 through the flexible walls of body 122 and manipulating member 130 until it is released from receiving port 124, thus causing it to move into the interior chamber defined by body 122. After disengaging the removable sealing member 130 from the receiving port 124, the second substance 108 is free to flow out of the opening 128 defined by receiving port 124.

Second substance 108 can be a variety of known substances, but in the embodiments described herein, second substance 108 is an IV-therapy fluid diluent known in the art (e.g., 0.9% Sodium Chloride). In alternative embodiments, second container 106 can be empty, and its contents are derived from the first container 102 (after connection with the first container 102 as described herein) or derived from an external source through a separate port or opening in second container 106.

FIGS. 4*a*-4*i* illustrate various exemplary embodiments of a connector 110 that can be used with the system 100 shown in FIG. 1. The connector 110 is configured such that it can be secured to the first container 102 and to the receiving port 124 of the second container 106.

The connector body 154 generally comprises three portions, a proximal portion 184, a middle portion 186, and a distal portion 188. In the exemplary embodiments of FIGS. 4*a*-4*i*, the proximal portion 184 has an average diameter that is greater than the average diameter of the middle portion 186, and the middle portion has an average diameter that is greater than the average diameter of the distal portion 188. The proximal portion 184 comprises a collar 190 that circumscribes the cavity 148 defined by connector body 154. Collar 190 can be substantially cylindrical, as depicted in the accompanying figures, or can have a variety of other configurations. As depicted herein, collar 190 can be provided with a surface geometry that allows a user to more easily grip and manipulate the connector 110 for securing it to the first and second containers. In the various embodiments shown in the figures, ratchet teeth 182 are annularly disposed on an outer surface 192 of the middle portion 186 of the connector body 154. The distal portion 188 defines a distal opening 168 of the connector 110 and is circumscribed by threads 177 extending from the distal portion's outer surface 178.

To facilitate securement of the connector 110 to the second container 106, the threads 177 are complementary to the threads 136 in the receiving port 124 of the second container 106. Additionally, the one-way ratchet teeth 182 are complementary to the one-way ratchet teeth 140 in the receiving port 124 of the second container 106. Engagement of the one-way ratchet teeth 140, 182 prevents the connector 110 from backing out once it has been threadably attached to the second container 106. In this example, the axial displacement between the threads 177 and the ratchet teeth 182 is such that during securement of the connector 110 to the second container 106, threaded engagement precedes ratchet engagement, however, in other embodiments, threaded and ratchet-teeth engagement may occur simultaneously. Herein, the threads 177 and ratchet teeth 182 of the connector 110 are collectively referred to as "securing mechanisms" of the connector. In various embodiments, only one of the securing mechanisms is used.

In an alternative configuration, ratchet teeth 182 can be formed as part of threads 177. In such a configuration, threads 177 and ratchet teeth 182 would be complementary to a similar configuration for threads 136 and ratchet teeth 140 in order to provide the desired securement of connector 110 to second container 106.

Figure 4A:
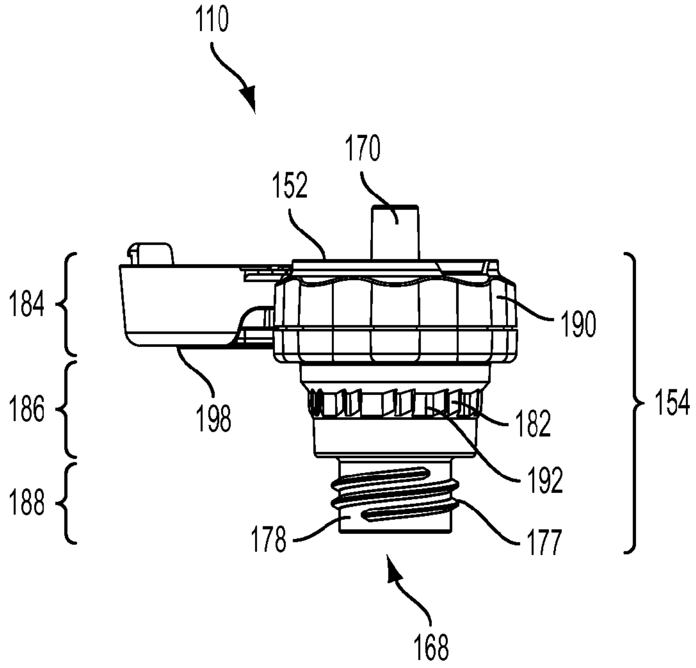
FIG. 4*a* illustrates a side view of an example connector that can be used with the system shown in FIG. 1.
Figure 4B:
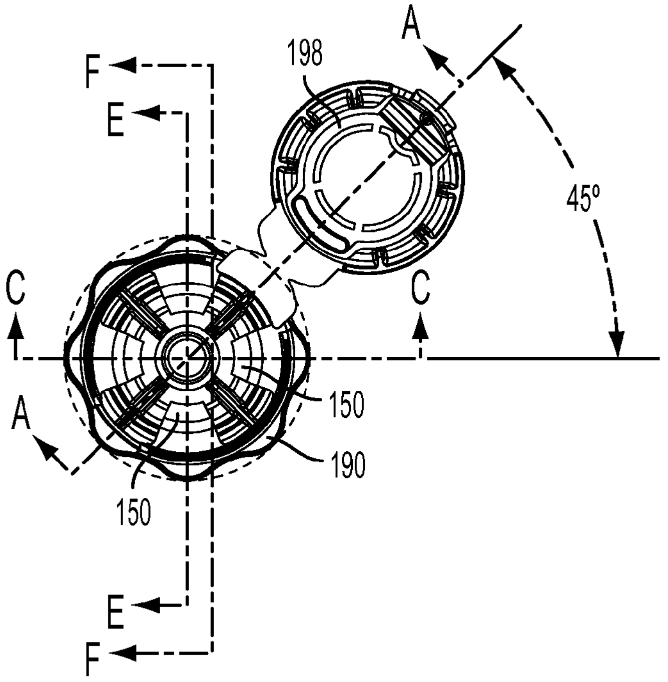
FIG. 4*b* illustrates a top view of the connector shown in FIG. 4*a*.
Figure 4C:
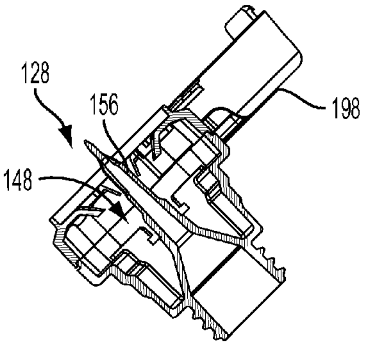
FIG. 4*c* illustrates a cross-sectional view of the connector shown in FIG. 4*a*.
Figure 4D:
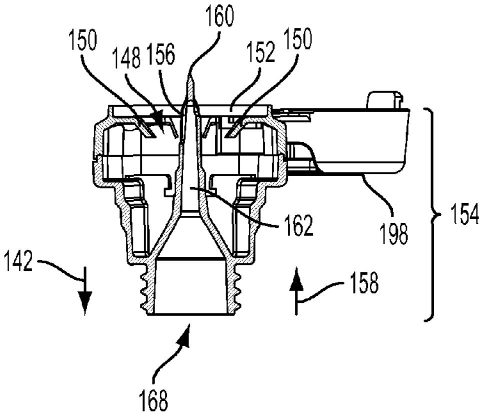
FIG. 4*d* illustrates another cross-sectional view of the connector shown in FIG. 4*a*.

As best shown in the cross-sectional views of the connector 110 illustrated in FIGS. 4*c* and 4*d*, the connector body 154 defines the cavity 148 configured to receive the distal end 116 of the first container 102. A retention member, shown as resilient retention fingers 150, is configured to engage the shoulder 117 of the first container 102. As shown, the fingers 150 extend distally and radially inwardly from the proximal end 152 of the connector body 154 such that they are positioned within the cavity 148. In this example, there are four fingers 150 substantially equally spaced around the axis of the connector 110 (see FIG. 4*b*). Any number of fingers, for example, two, three or four, are appropriate as long as they secure the first container 102 to the connector 110. In one embodiment, the retention member includes s a single, resilient annular ring that uniformly collars and engages the entire neck portion 114 of the first container 102.

The fingers 150 are configured to prevent removal of the first container 102 from the connector 110 after the distal end 116 of the first container 102 is inserted a predetermined distance into the cavity 148. As with the engagement between the connector 110 and second container 106, with a sufficient amount of force, the first container 104 can be separated from the connector 110 but not without visibly damaging the connector and/or first container. The predetermined distance required to engage the first container 104 with the connector 110 corresponds to the amount of insertion required for the fingers 150 to engage shoulder 117 of the first container 102. By preventing removal of the first container 102 from the connecter 110, drug tampering and contamination, and accidental discharge of the substances 104, 108 caused by container-connector disengagement, is prevented.

In another embodiment of the retention fingers 150 shown in FIGS. 6*a*-*d*, each retention finger 150 is attached to the connector body 154 via two tabs 208 (as opposed to being attached via the entire arc length of the retention finger 150 as show in FIG. 4*b*) that form a slit 210 therebetween. Although only two tabs 208 are shown, other embodiments may include more than two tabs 208 to attach each retention finger 150 to the connector body 154. In such an embodiment, a separate slit 210 would be formed between each set of two adjacent tabs 208. The tabs 208 function as a living hinge for their respective retention finger 150. Such a configuration requires less force to engage the first container 104 and the connector 110 ("the insertion force") than the embodiment of the fingers 150 shown in FIG. 4*b*.

The vertical (or axial oriented) thickness of each tab 208 may be equal to or less than the thickness of the retention finger 150. In an embodiment utilizing tabs 208 that are thinner than the retention fingers 150, the insertion force required to engage the first container 104 and the connector 110 is decreased due to increased flexibility of the fingers 150 at the tabs 208. In addition, the width W1 of the tabs 208 may be minimized to further reduce the insertion force. In one embodiment, the width W1 of the tabs 208 is between 0.1-0.15 inches. In another embodiment the width W1 may be 0.125 inches.

In the embodiment shown in FIG. 4*b*, the insertion force may be between 25-45 lbf, however, in the tab/slit configuration shown in FIGS. 6*a*-*d*, the insertion force may be reduced to somewhere between 10-20 lbf, a significant amount of which is the force required to cause penetrating member 156 to pierce seal 120 of the first container 104. In one embodiment the retention fingers 150 may only account for about 0.5-3 lbf of the required insertion force. In other embodiments, the retention fingers 150 may account for about 0.5-10 lbf of the required insertion force.

Moreover, the tab/slit configuration can provide a visual indication in the event that the first container 104 is removed from the connector 110 because in such an event, the tabs 208 attaching the retention fingers 150 to the connector 110 tend to break or fracture, thus inhibiting ill-advised reuse of the connector 110. The geometry of the slits 210, including their width W2 and arc length, may change from that shown in FIG. 6*c*. The greater arc length of the slit 210 relative to the width W2 of the tabs 208, the greater the finger flexibility and the smaller the required insertion force. In one embodiment, the arc length of the slit 210 may be between 0.4-0.6 inches and the width W2 of the slit 210 may be between 0.04-0.06 inches.

Figure 7B:
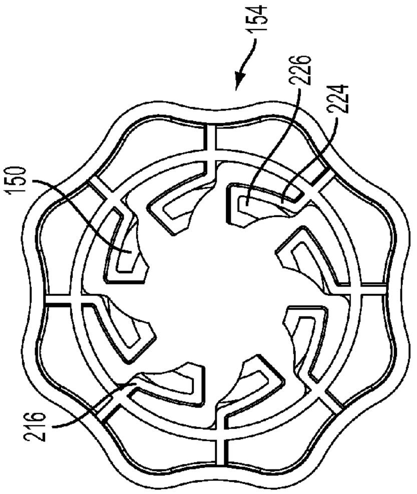
FIG. 7*b* illustrates a bottom view of the embodiment of the retention members shown in FIG. 7*a*.
Figure 7C:
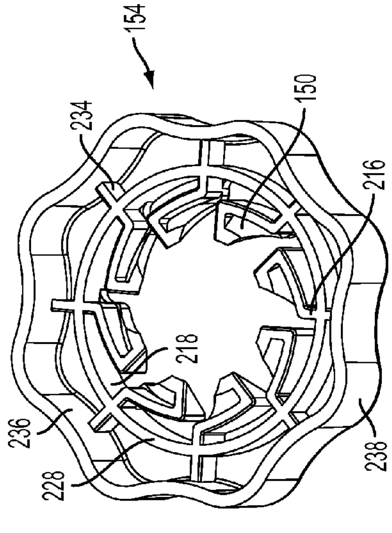
FIG. 7*c* illustrates an isometric view of the embodiment of the retention members shown in FIG. 7*a*.
Figure 7A:
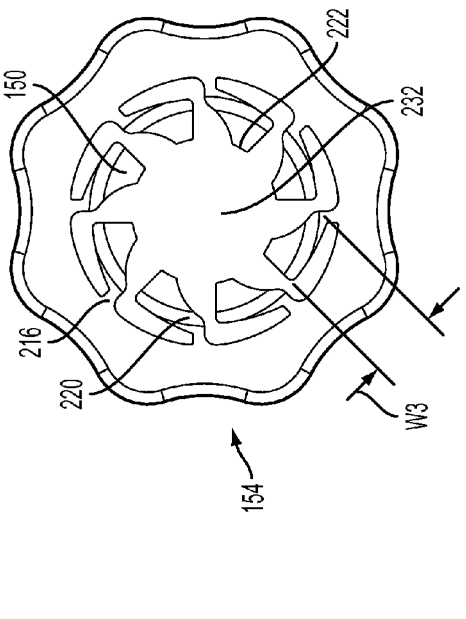
FIG. 7*a* illustrates a top view of an embodiment of retention members of a connector that can be used in the system shown in FIG. 1.

In another embodiment of the retention fingers 150 shown in FIGS. 7*a*-*c*, each retention finger 150 is attached to the connector body 154 via a single connecting arm 216 that extends from surface 218. In such an embodiment, a retention finger 150 can rotate about two axes, up and down about an axis perpendicular to the direction in which the first container 104 is inserted, and side to side about an axis parallel the direction in which the first container 104 is inserted. This is in contrast to the embodiments shown in FIGS. 4*b* and 6*c* which only allow the retention finger 150 to rotate up and down about an axis perpendicular to the direction in which the first container 104 is inserted. Such increased mobility of the retentions fingers 150 helps to decrease the required insertion force. Moreover, the geometry of the retention fingers 150 shown in FIGS. 7*a*-*c*, wherein the width W3 of the retention finger decreases along its length from its proximal end 220 near the connecting arm 216 to its distal end 222, further decreases the required insertion force for the first container 104.

In the embodiment shown in FIGS. 7*a*-*c*, the structural integrity of the retention fingers 150 has been increased by providing a rib 224 that extends about a portion of the periphery of the distal surface 226 of the retention finger 150. As shown best in FIG. 7*c*, further structural integrity can be obtained by providing an annular rib 228 that extends about the underside of the periphery of the opening 232 at the point where the connecting arm 216 is attached to the connector body 154 and by providing radial ribs 234 that extend from the inside surface 236 of the collar 238 of the connector body 154 to the annular rib 228.

In addition to preventing removal of the first container 104 from the connector 110, the connector 110 is configured to prevent over-insertion of the first container 104 after it is engaged with the connector 110 via the retention fingers 150. As shown best in the connector illustrated in FIGS. 4*g* and 5*e*, the connector is provided with vertical ribs 212 that extend from an internal surface 214 of the connector 110 to a proximal position below the fingers 150. Any number of ribs 212 is possible. The distance between the ribs 212 and the fingers 150 is such that the shoulder 117 of the first container 104 rests between the ribs 212 and fingers 150 after engagement of the first container 104 and connector 110. The ribs 212 prevent the first container 104 from moving past a certain point in the distal direction 142 and provide a tactile stop for the user. In another embodiment, as shown best in FIG. 6*b*, the connector 110 is provided with an annular ring 214 that serves the same function as the ribs 212 of the embodiment shown in FIGS. 4*g* and 5*e*.

To provide fluid communication between the contents of one container and the other, a hollow penetrating member 156 that is radially inwardly (or laterally) offset from the fingers 150 is provided. The penetrating member 156 extends in the proximal direction 158 from a generally centrally-located (or substantially axial) position within the cavity 148 to a position near the proximal end 152 of the connector body 110. The penetrating member may extend beyond the proximal end 152 of the connector. The penetrating member 156 is configured to pierce the seal 120 of the first container 102. Accordingly, the proximal end 160 of the penetrating member 156 is pointed. As first container 102 is moved into cavity 148, penetrating member 156 penetrates seal 120 of the first container, and when first container 102 has been inserted the predetermined distance within cavity 148 (i.e., the distance at which fingers 150 engage shoulder 117 of first container 102), penetrating member 156 has fully penetrated seal 120 in order to provide fluid access to contents 104, as described in greater detail below.

Figure 4E:
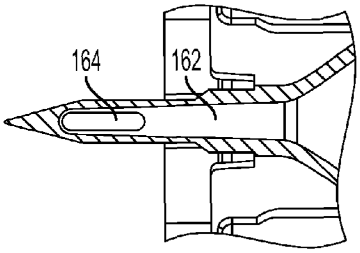
FIG. 4*e* illustrates a cross-sectional view of the penetrating member of the connector shown in FIG. 4*a*.
Figure 4F:
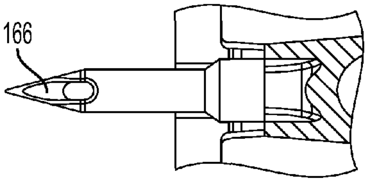
FIG. 4*f* illustrates the penetrating member of the connector shown in FIG. 4*a*.

In the embodiment depicted in FIGS. 4*e* and 4*f*, first and second apertures 164, 166 are located near the proximal end 160 of the penetrating member 156. First and second apertures 164, 166 provide fluid communication between an external environment of penetrating member 156 and a flow passageway 162 defined axially through penetrating member 156. As shown, the penetrating member 156 comprises two apertures 164, 166, where aperture 164 is larger than aperture 166. Embodiments of penetrating member 156 can include one, two, three, or more such apertures, and these apertures can be of a variety of sizes and shapes. Where penetrating member 156 includes two or more apertures, the apertures can be of the same or different geometries, and the two or more apertures can be of the same or different size.

In the embodiment depicted in FIGS. 4*e* and 4*f*, two apertures 164, 166 are provided and are configured as longitudinal slots running substantially parallel to the axis of penetrating member 156. In the depicted embodiment, aperture 164 is longer in length than aperture 166. The additional length of aperture 164 is selected such that aperture 164 provides fluid communication between flow passageway 162 and an interior of vial 102 at a point relatively close to, or substantially flush with, the interior surface of seal 120. The positioning of the lower end (i.e., distal end) of first aperture 164 substantially adjacent to the interior surface of seal 120 will facilitate the flow of all, or substantially all, of the contents of vial 102 into second container 106 by reducing or eliminating the possibility of a dead space therebetween. In the embodiment of penetrating member 156 depicted in FIGS. 4*e* and 4*f*, the lower end of second aperture 166 is spaced from the interior surface of seal 120 when the vial is inserted into the connector. This construction provides greater structural integrity to penetrating member 156 by increasing the amount of material used in constructing the penetrating member 156. It will be appreciated that as the total surface area of penetrating member 156 occupied by apertures 164, 166 increases (i.e., by increasing the length, width, and/or number of apertures), the structural integrity of member 156 will tend to decrease, particularly when it is constructed from a plastic material.

The flow passageway 162 is defined through the penetrating member 156 and fluidly connects with the distal opening 168 of the connector 110, thereby providing fluid communication between the apertures 164, 166 and the distal opening 168. The cross-sectional area of flow passageway 162 is preferably selected to be as large as possible in order minimize flow resistance and maximize flow volume through flow passageway 162. This will minimize the amount of force or "milking" necessary in order to move fluids into and out of vial 102.

Figure 4G:
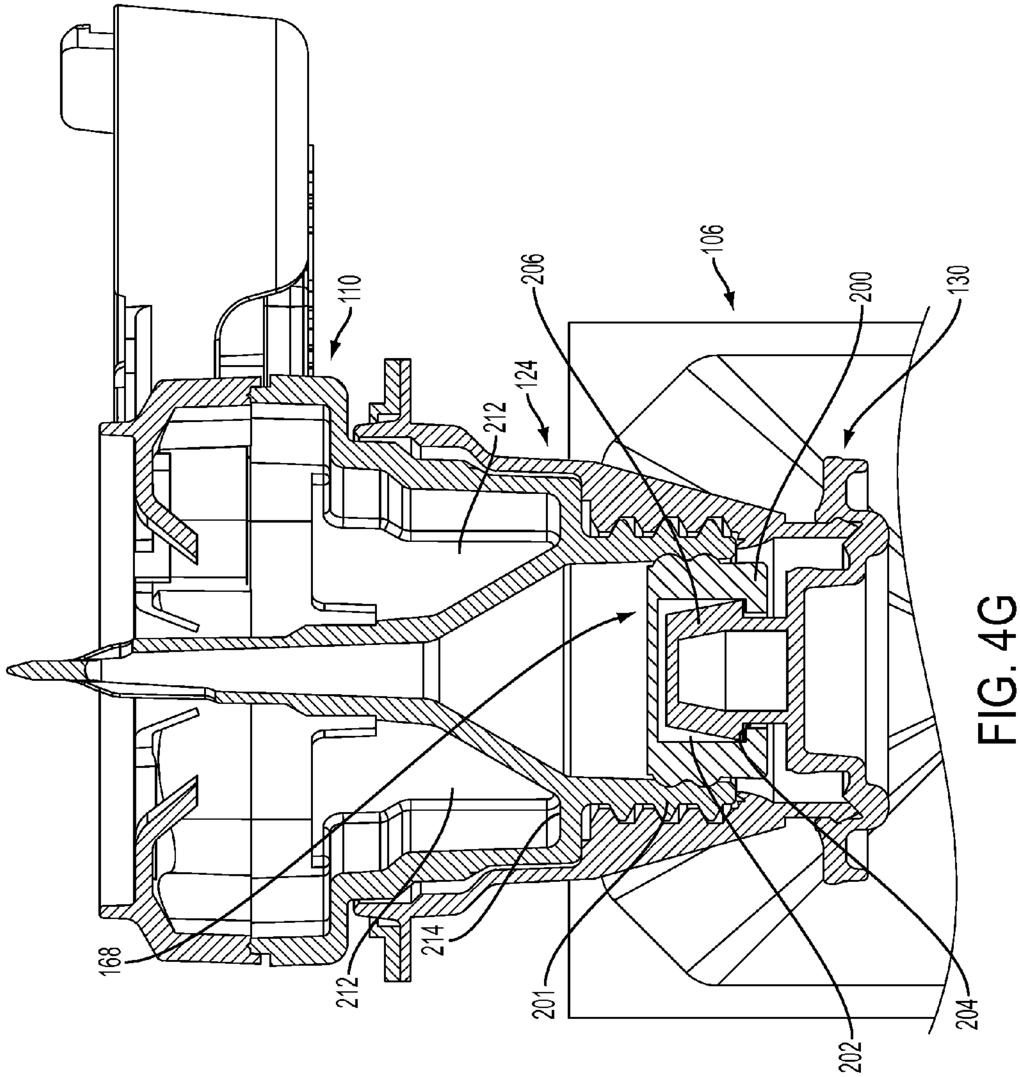
FIG. 4*g* illustrates a cross-sectional view of another example connector that can be used in the system shown in FIG. 1.
Figure 4H:
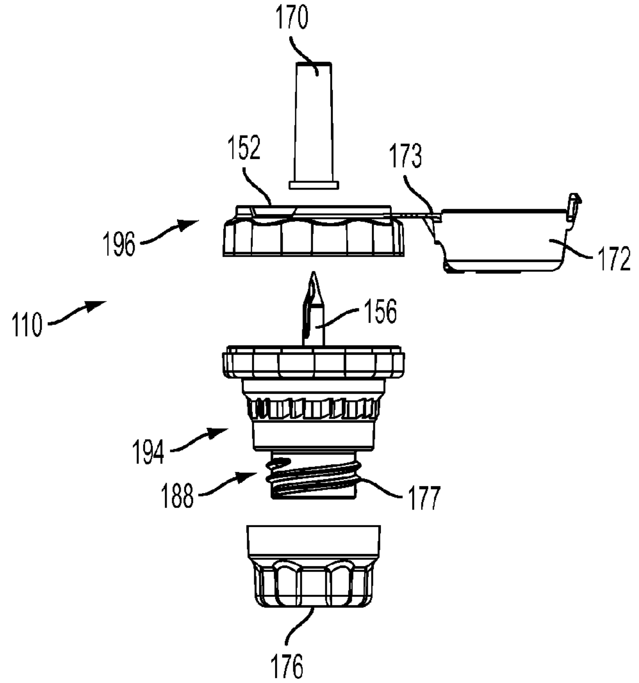
FIG. 4*h* illustrates an exploded view of the connector shown in FIG. 4*a*.

In a further embodiment of the connector 110 shown in FIG. 4*g*, the connector 110 includes a removable plug 200 secured (e.g., a press or frictional fit engagement, snap fitment engagement, etc.) in the neck portion 201 of the connector that defines the distal opening 168. The removable plug 200 is configured to engage the removable sealing member 130 of the second container 106. The removable plug 200 may be made of a material capable of providing a substantially fluid-tight seal of neck portion 201 of connector 110. A variety of elastomeric materials, particularly elastomeric materials used in the pharmaceutical industry, can be used. The removable plug 200 provides sterility of the interior of connector 110 prior to use and also prevents flow of the first substance 104 through the connector until the plug is removed. This prevents the accidental release of the substance 104 from the first container 102 in the event that the first container is secured to the connector 110 before the second container 106 is secured to the connector 110. This is beneficial because it eliminates the need to secure the first and second containers 102, 106 to the connector 110 in any particular order. However, if removable plug 200 is not present, it will be appreciated that it will be preferable to attach connector 110 to second container 106 prior to attaching connector 110 to vial 102, thereby preventing accidental spillage of contents 104 of vial 102 and maintaining the sterility of contents 104.

As shown in FIG. 4*g*, the removable plug 200 has a recess 202 with an undercut shoulder 204 for engaging a plug removing feature 206 of the removable sealing member 130. Thus, as the connector 110 is advanced into and engaged with the receiving port 124 of the second container 106, the removable plug 200 of the connector advances onto the plug removing feature 206. Plug removing feature 206 is either integrally formed with, or connected to, the removable sealing member 130. The plug removing feature 206 engages the removable plug 200 such that the removable plug may subsequently be removed from the connector by pulling or pushing on the removable sealing member 130 in the distal direction 142 as described above.

Prior to securing the first or second containers 102, 106 to the connector 110, it is desirable to maintain sterility of the connector by preventing contamination of the connector and its various components. Therefore, in addition to the removable plug 200 (which is not present in all embodiments of the connector 110), the connector 110 may include a cap 170 (see FIGS. 4*a*, 4*h*, 6*a*, and 6*b*) for the penetrating member 156 and/or a proximal end cap 172 (see FIGS. 4*a*-*d* and 4*g*-6*d*). If both proximal end cap 172 and cap 170 are present, they can be integrally formed, attached to one another, or entirely separate. In one embodiment, the proximal end cap 172 and penetrating member cap 170 are separate components that do not touch in the assembled configuration.

Cap 170 is provided in order to maintain sterility of penetrating member 156 prior to use and must be completely removed from penetrating member 156 before a vial 102 can be inserted into the connector. Proximal end cap 172 is provided in order to protect penetrating member 156 and to prevent the ingress of contaminants (including dust) into the interior of connector body 154 prior to use. Proximal end cap 172 can be a separate and completely detachable structure or it can be hingedly attached (e.g., via a living hinge 173, a flexible band, a pin joint, etc.) to connector body 154 such that it can be swung open. In addition, proximal end cap 172 can be injection-molded with connector body 154 such that proximal end cap 172 is frangibly connected to connector body 154 prior to use. However, the frangible connection between cap 172 and connector body 154 must allow for easy removal of cap 172 from connector body 154 in order for a user to remove the cap prior to use.

The distal portion 188 of the connector 110 may also be provided with an end cap 176. End cap 176 may be threaded for engagement with threads 177 of the connector 110. Additionally or alternatively, end cap 176 may be configured for a snap and/or press fit attachment to the distal portion 188 of the connector 110. In other examples, the distal end 174 of the connector 110 may be provided with a different type of cover.

For instance, the distal end 174 of the connector 110 may come with a seal or septum that can be pealed off or pierced by the user prior to use.

Figure 4I:
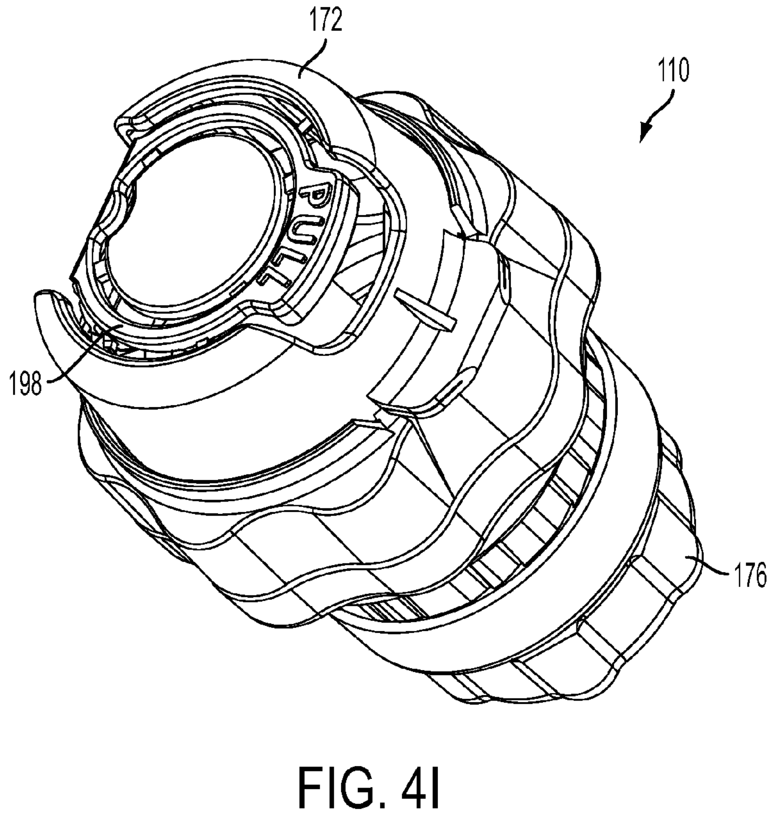
FIG. 4*i* illustrates an isometric view of the connector shown in FIG. 4*a*.

As best shown in FIG. 4*i*, the connector 110 may also include a ring 198 for hanging the system 100 during use. As shown, the ring 198 may be part of the end cap 172 and may include a pull tab that allows a user to swing open the ring 198, away from the cap 172, before or after the cap 172 has been swung open from the body of the connector 110. In such an embodiment, the ring 198 may be attached to the cap 172 by a flexible strap, a living hinge, a pin joint, etc. that allows the ring 198 to swing open and be presented for use. In addition, prior to use, the ring 198 may be frangibly attached to the cap 172 by one or more frangible posts that are fractured when the ring 198 is swung open. In another embodiment (which is not shown), the ring 198 may be attached directly to the proximal end 152 of the connector 110 such that it is able to snap onto or rest on the proximal end 152 of the connector body 154 when the ring is not being used. Such an attachment may be accomplished with a flexible strap, a living hinge, a simple pin joint, etc. In an alternative embodiment, such as the one shown in FIGS. 6*a-d*, a hanging ring 198 can be an integral part of the end cap 172 such that it cannot be manipulated relative to cap 172. In such an embodiment, once the end cap 17 is swung open from the body of the connector 110, the ring 198 is ready for use without any additional manipulation by the user.

Both of the end caps 172, 176 may be provided with anti-tamper features to prevent inadvertent removal. For example, each end cap 172, 176 may be attached to the connector body 154 via a frangible feature such as a post or weld, or a snap fit known in the art. In an embodiment using a frangible feature such as a post or weld, the post or weld would need to be fractured in order to remove the end cap. Such an embodiment provides tactile and visual feedback to the user that the end cap has been removed. In an embodiment using a snap fit connection, the user must disengage the snap fit which also provides tactile feedback.

The connector body 154 may be a single unitary part or may be constructed from more than one part. For instance, as shown best in FIG. 4*h*, the connector may be two parts 194, 196 that can be fixed together by threads, press fit, adhesive, heat welding, snap fit, etc., or some combination. This two-part design may be beneficial from a manufacturing perspective. Regardless of whether the connector is one or more parts, the connector 110 may be made of relatively rigid plastic materials that are known to be inert to pharmaceutical formulations.

B. Operation

The system 100 allows a user to attach the first container 102 to the second container 106 with the ability to establish fluid communication between the containers at a subsequent time. This is important because of the limited shelf-life of some substances once they have been mixed or reconstituted with another substance. Therefore, the system 100 allows, for example, a pharmacist to securely connect the first container 102 to the second container 106 in a permanent manner without establishing fluid communication between the containers. A nurse or other practitioner can then establish fluid communication between the containers at a patient's bedside by removing the sealing member 130 from the receiving port 124 the second container 106.

Figure 5A:
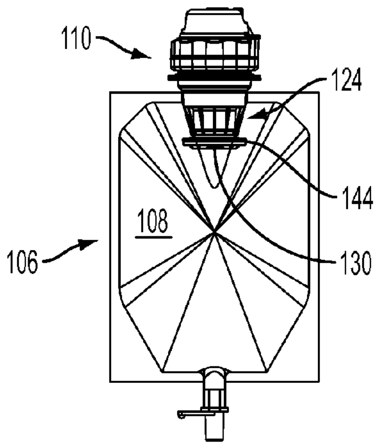
FIG. 5*a* illustrates the first step of an exemplary method for intermixing at least two substances.
Figure 5B:
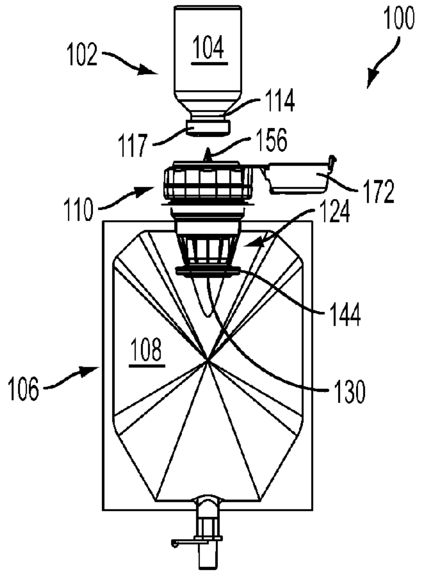
FIG. 5*b* illustrates the second step of an exemplary method for intermixing at least two substances.
Figure 5C:
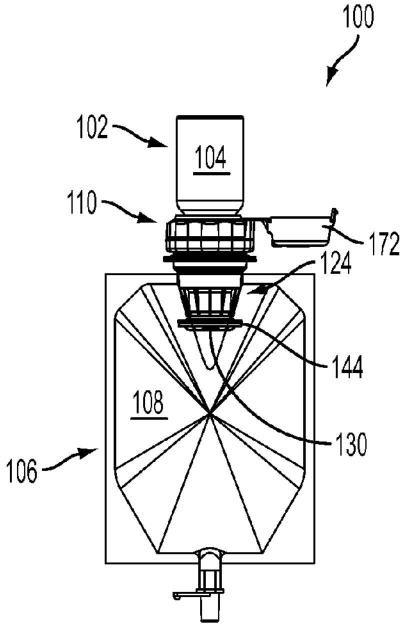
FIG. 5*c* illustrates the third step of an exemplary method for intermixing at least two substances where the connector does not include a removable plug.
Figure 5D:
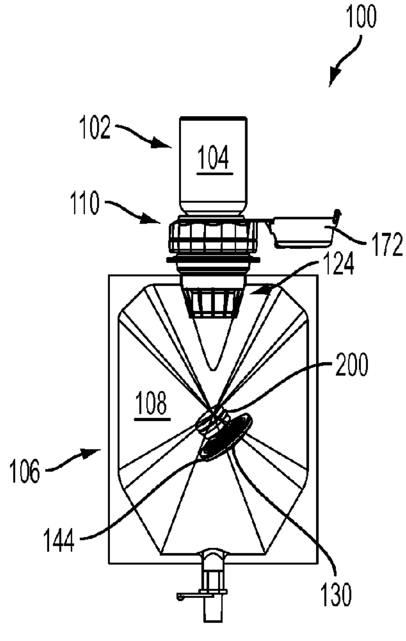
FIG. 5*d* illustrates the third step of an exemplary method for intermixing at least two substances where the connector includes a removable plug.
Figure 5E:
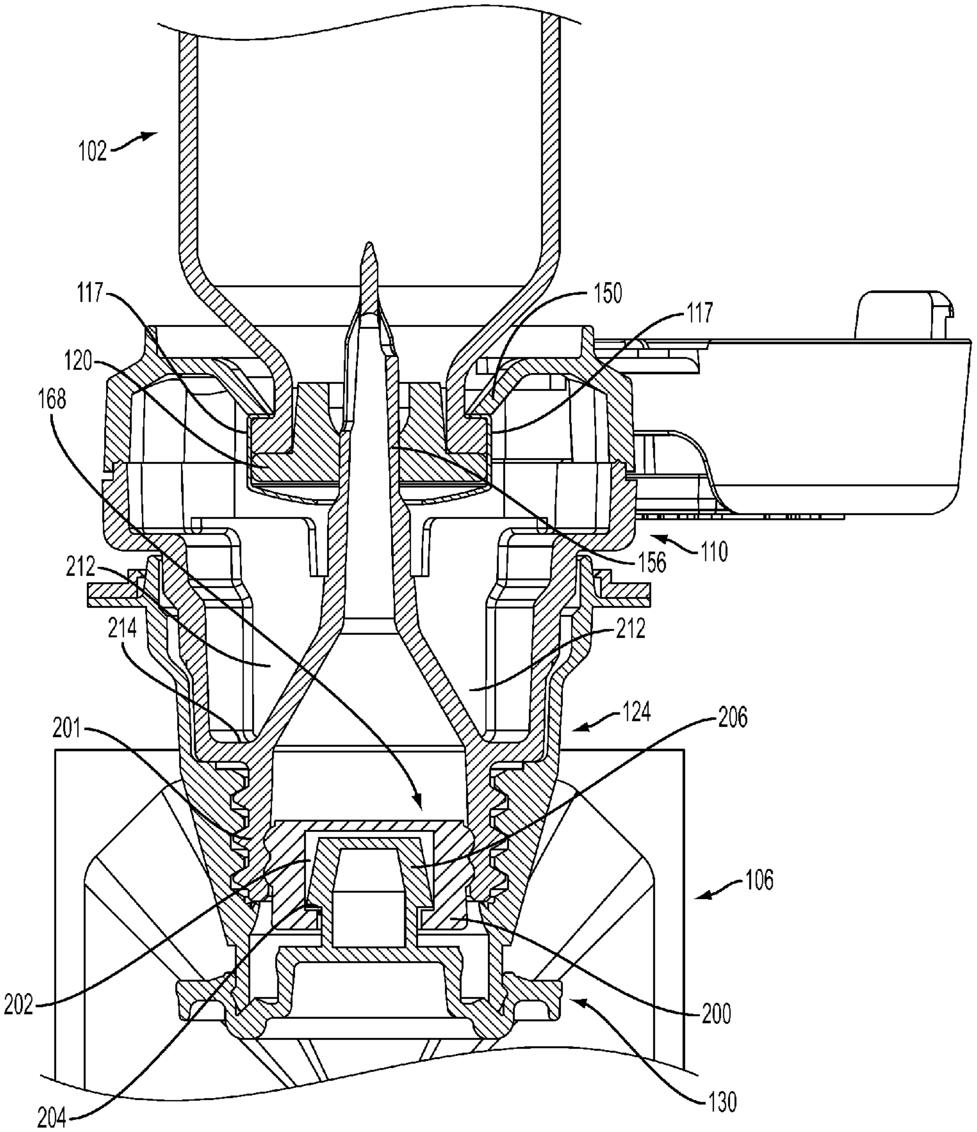
FIG. 5*e* illustrates a cross-sectional view of the penetrating member of the connector piercing the seal of the first container during the second step of the method shown in FIG. 5*b*.
Figure 6B:
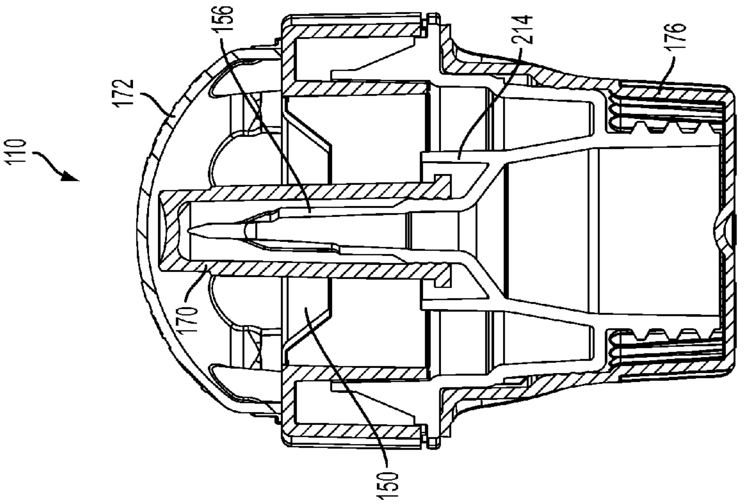
FIG. 6*b* illustrates a cross-sectional view of the connector of FIG. 6*a*.
Figure 6A:
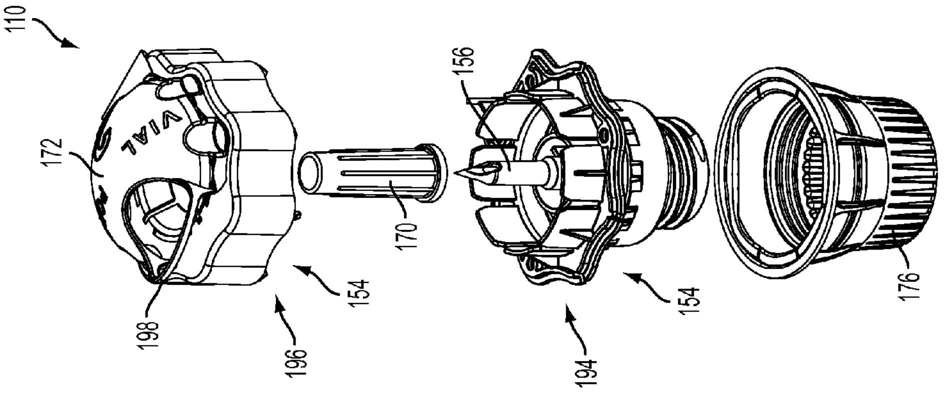
FIG. 6*a* illustrates an exploded view of another example connector that can be used in the system shown in FIG. 1.
Figure 6D:
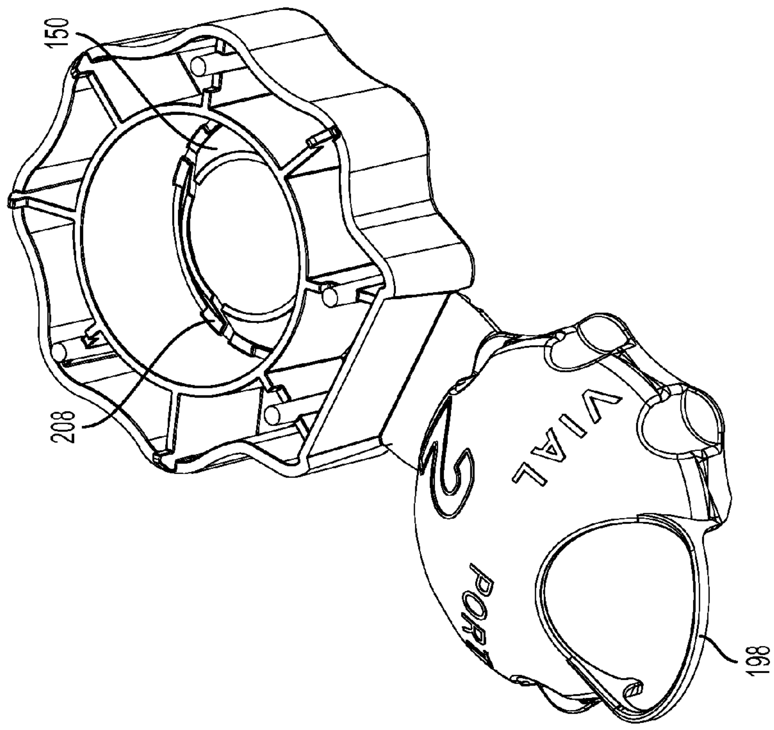
FIG. 6*d* is an isometric bottom view that illustrates the retention members of the connector of FIG. 6*a*.
Figure 6C:
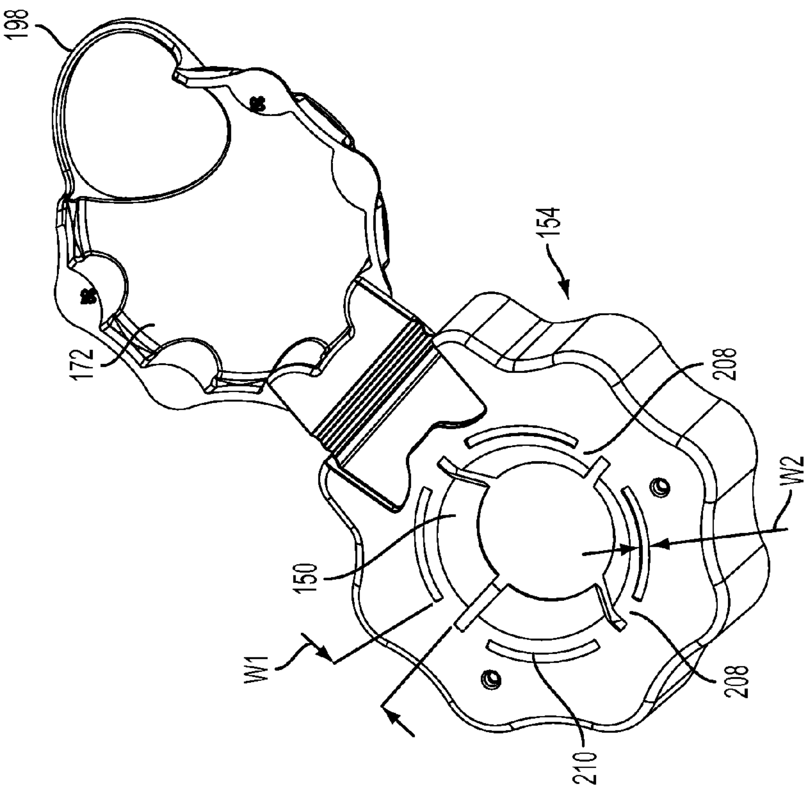
FIG. 6*c* is an isometric top view that illustrates the retention members of the connector of FIG. 6*a*, where each retention member is connected to the body of the connector via two tabs forming a slit therebetween.

FIGS. 5*a*-5*e* illustrate an exemplary method for intermixing the contents of two containers using system 100. FIG. 5*a* illustrates the first step of the method which involves securing the second container 106 to the connector 110. When the connector 110 does not include a removable plug 200, it is preferable to secure the second container 106 to the connector 110 before securing the first container 102 to the connector 110 because, in this case, the connector 110 does not have any means for preventing flow through the flow passageway 162 of the penetrating member 156 and out of the distal opening 168 of the connector 110. If the first container 102 is secured to the connector 110 prior to the second container 106, then the first substance 104 may flow out of the first container 102 and through the connector 110 via the flow passageway 162, thereby potentially exposing the user to hazardous material or spilling the contents of first container 102. Of course, it is also possible that this will result in external contaminants flowing into first container 102 through connector 110. However, as noted above, where the connector 110 includes a removable plug 200, the order in which the first and second container 102, 106 are secured to the connector is irrelevant.

To secure the second container 106 to the connector 110, the user inserts the distal threaded portion 188 of the connector 110 into the receiving port 124 of the second container 106. Once contact is made between the complementary threads 136, 177 of the connector 110 and second container 106, the user rotates the connector in the clockwise direction, thereby screwing the connector to the second container.

After the distal threaded portion of the connector 110 is screwed a predetermined axial distance into the receiving port 124 of the second container 106, the complementary one-way ratchet teeth 140, 182 of the connector and second container begin to engage. The user continues to screw the connector 110 into the second container 106 until further axial displacement is no longer possible without damaging the threads and/or ratchet teeth of the container and/or connector. At a threshold axial engagement of the ratchet teeth 140, 182, the connector 110 is prevented from backing-out of the receiving port 124. Where the connector 110 is provided with a removable plug 200, the removable plug 200 of the connector preferably simultaneously advances onto and engages the plug removing feature 206 of the removable sealing member 130 while the user screws the connector 110 into the second container 106 (see FIG. 4*g*).

FIGS. 5*b* and 5*c* illustrate the second step of the exemplary method, which involves securing the first container 102 to the connector 110. Prior to securing the first container 102 to the connector 110, cap 170 and proximal end cap 172 must be removed. To secure the first container 102 to the connector 110, the user axially aligns the two devices and moves them together in such a way that the penetrating member 156 begins to pierce the seal 120 of the first container 102. As the seal 120 is pierced, the neck portion 114 of the first container 102 is simultaneously moving into the cavity 148 of the connector 110. The user continues to move the first container 102 and the connector 110 toward one another until the fingers 150 of the connector 110 latch onto the shoulder 117 of the first container 102 (see FIG. 5*e*). At the point at which fingers 150 are secured to shoulder 117, penetrating member 156 has fully penetrated seal 120, thereby providing fluid communication between the interior of first container 102 and flow passageway 162 through apertures 164, 166. The user will be prohibited from over-inserting the first container 104 and damaging the container and/or connector by vertical ribs 212 or annular ring 214.

The radially inward and distally extending configuration of the fingers 150 centers the first container 102 in the connector 110. Once the fingers 150 latch onto the shoulder 117 of the first container 102 (i.e., when the proximal surface of the shoulder passes the distal surface or edge of the finger), removal of the first container 102 from the connector 110 is prevented or at least made very difficult without causing damage to the first 102 container and/or connector 110.

After first container 102 has been connected to connector 110, fluid communication between the first and second containers 102, 106 (via the connector 110) is prevented by the removable sealing member 130 alone, or by the removable sealing member 130 in combination with removable plug 200, depending on whether the connector 110 includes a removable plug 200.

Where it is desirable for the user to connect the connector 110 to the second container 106 first, the various protective caps 170, 172, 176 may be provided with numbers that correspond to the order of steps that the user is supposed to take. For example, the distal end cap 176 may be provided with the number 1, which signals to the user that the distal end cap 176 should be removed first and then the second container 106 should be connected to the connector 110. The proximal end cap 172 may be provided with the number 2, which signals to the user that the proximal end cap 172 should be removed second. Finally, the penetrating member cap 170 may be provided with the number 3, which signals to the user to remove the cap 170 third. The first container 104 can now be connected to the connector 110 and intermixing can ensue.

FIG. **5*d* illustrates the third step of the exemplary method, which involves disengagement/removal of the sealing member 130 from the receiving port 124 of the second container 106, with FIG. 5*d* corresponding the case where the connector includes a removable plug 200**.

In the case where the connector 110 does not include a removable plug 200, to remove the sealing member 130, the user externally manipulates the flexible walls of second container 106 until the user can grasp the flange 144 of the sealing member. Once the user can grasp the flange 144, the user pulls, pushes, or flips down (i.e., in the distal direction 142) on the flange until the force is great enough to overcome the force securing the sealing member 130 to the receiving port 124, thereby disengaging the sealing member from the receiving port. If the connector 110 includes the removable plug 200 as shown in FIG. **5*d*, the plug 200 is pulled into the second container 106 along with the sealing member 130 to which it is now attached. After disengagement, the user may release the sealing member 130 into the body or interior 122 of the second container 106. Fluid communication between the first container 102 and the second container 106 (via the flow channel 162) is now enabled. Depending on the orientation of the system 100 and the characteristics of the substances 104, 108, intermixing may immediately commence. However, in order to sufficiently intermix the substances 104, 108, the user may have to invert or tip the system 100, shake the system 100, and/or squeeze/milk either or both of the containers 102, 106. Once the substances 104, 108 are intermixed, the composition may be delivered to a patient through outlet 132. Ring 198 is provided to allow a healthcare professional to hang the system from a hanger such as a standard IV pole. Delivery of the contents of first container 102 and second container 106 to the patient will require that an IV line of known construction be fluidly connected to outlet 132 of second container 106**.

Various embodiments of the system (including its components) and corresponding method for intermixing at least two substances have been described above. Those skilled in the art will understand, however, that changes and modifications may be made to those embodiments without departing from the scope of the claims.

We claim:

1. A system for intermixing the contents of two containers, the system comprising:

(i) a first container comprising a pierceable seal for sealing an opening in a distal end portion of the first container, wherein the first container contains a first substance;

(ii) a second container having a wall constructed of a flexible material, the second container comprising (a) a receiving port comprising a first securing mechanism on an inner surface thereof, and (b) a removable sealing member for sealing the receiving port, the removable sealing member constructed to be movable between a first, sealed position and a second, unsealed position, the removable sealing member being movable through manual manipulation of the removable sealing member through the wall constructed of the flexible material, wherein the removable sealing member is positioned within an interior chamber of the second container when the removable sealing member is in the second, unsealed position, wherein the second container contains a second substance; and (iii) a connector for connecting the first and second containers, the connector comprising:

(a) a proximal end portion defining a cavity configured to receive the distal end portion of the first container, the proximal end portion including a penetrating member axially fixed within the cavity defined by the proximal end portion, the penetrating member defining a fluid flow passageway, the penetrating member having a proximal end portion constructed to penetrate the pierceable seal of the first container when the distal end portion of the first container is inserted into the cavity defined by the proximal end portion of the connector, the proximal end portion further including at least one resilient retention member constructed to retain the distal end portion of the first container in the cavity defined by the proximal end portion of the connector when the distal end portion of the first container is inserted therein;

(b) a distal end portion configured for insertion into the receiving port of the second container, the distal end portion of the connector having a complementary securing mechanism constructed to engage the first securing mechanism of the second container whereby the first and complementary securing mechanisms retain the distal end portion of the connector in the receiving port, the distal end portion further defining a distal opening of the connector, the distal opening of the connector being in fluid communication with the fluid flow passageway defined by the penetrating member so as to define a fluid flow channel through the connector; and (c) a removable plug positioned in the fluid flow channel through the connector, the removable plug configured to substantially fluidly seal the fluid flow channel through the connector.

2. The system of claim 1, wherein the removable plug of the connector is constructed to securely engage the removable sealing member of the second container when the distal end portion of the connector is inserted into the receiving port of the second container, and wherein the removable plug is configured to be moved from a first position in which it substantially fluidly seals the fluid flow channel through the connector to a second, unsealed position when the removable sealing member of the second container is moved from its first, sealed position to its second, unsealed position.

3. The system of claim 2, wherein the removable plug of the connector includes a recess with an undercut for securely engaging the removable sealing member of the second container.

4. The system of claim 1, wherein the first securing mechanism on the second container comprises a set of ratchet teeth and wherein the complementary securing mechanism on the connector comprises a complementary set of ratchet teeth.

5. The system of claim 1, wherein the at least one resilient retention member is attached to the body of the connector via at least two tabs.

6. The system of claim 5, wherein at least one of the at least two tabs is constructed to break if the first container is detached from the connector.

7. A method for intermixing the contents of a first container and a second container, the method comprising:

providing the system of claim 1;

connecting the first and second containers to the connector;

removing the removable sealing member of the second container by manually manipulating the removable sealing member through the wall of the second container; and intermixing the first and second substances.

8. The method of claim 7, wherein the second container is connected to the connector before the first container is connected to the connector.

9. The method of claim 7, wherein the first container is connected to the connector before the second container is connected to the connector.

10. The system of claim 1, wherein the first securing mechanism on the second container comprises a thread and wherein the complementary securing mechanism on the connector comprises a complementary thread.

11. A system for intermixing the contents of two containers, the system comprising:

(i) a first container comprising a pierceable seal for sealing an opening in a distal end portion of the first container, wherein the first container contains a first substance;

(ii) a second container having a wall constructed of a flexible material, the second container comprising (a) a receiving port comprising a first securing mechanism on an inner surface thereof, and (b) a removable sealing member for sealing the receiving port, the removable sealing member constructed to be movable between a first, sealed position and a second, unsealed position, the removable sealing member being movable through manual manipulation of the removable sealing member through the wall constructed of the flexible material, wherein the removable sealing member is positioned within an interior chamber of the second container when the removable sealing member is in the second, unsealed position, wherein the second container contains a second substance; and (iii) a connector for connecting the first and second containers, the connector comprising:

(a) a proximal end portion defining a cavity configured to receive the distal end portion of the first container, the proximal end portion including a penetrating member positioned within the cavity defined by the proximal end portion, the penetrating member defining a fluid flow passageway, the penetrating member having a proximal end portion constructed to penetrate the pierceable seal of the first container when the distal end portion of the first container is inserted into the cavity defined by the proximal end portion of the connector, the proximal end portion further including at least one retention member constructed to retain the distal end portion of the first container in the cavity defined by the proximal end portion of the connector when the distal end portion of the first container is inserted therein;

(b) a distal end portion configured for insertion into the receiving port of the second container, the distal end portion of the connector having a complementary securing mechanism constructed to engage the first securing mechanism of the second container whereby the first and complementary securing mechanisms retain the distal end portion of the connector in the receiving port, the distal end portion further defining a distal opening of the connector, the distal opening of the connector being in fluid communication with the fluid flow passageway defined by the penetrating member so as to define a fluid flow channel through the connector; and (c) a removable plug positioned in the fluid flow channel through the connector, the removable plug configured to substantially fluidly seal the fluid flow channel through the connector.

12. The system of claim 11, wherein the removable plug of the connector is constructed to securely engage the removable sealing member of the second container when the distal end portion of the connector is inserted into the receiving port of the second container, and wherein the removable plug is configured to be moved from a first position in which it substantially fluidly seals the fluid flow channel through the connector to a second, unsealed position when the removable sealing member of the second container is moved from its first, sealed position to its second, unsealed position.

13. The system of claim 12, wherein the removable plug of the connector includes a recess with an undercut for securely engaging the removable sealing member of the second container.

14. The system of claim 11, wherein the first securing mechanism on the second container comprises a set of ratchet teeth and wherein the complementary securing mechanism on the connector comprises a complementary set of ratchet teeth.

15. The system of claim 11, wherein the at least one retention member on the proximal end portion of the connector is a resilient latching retention member that is attached to the body of the connector via at least two tabs.

16. The system of claim 15, wherein at least one of the at least two tabs is constructed to break if the first container is detached from the connector.

17. The system of claim 11, wherein the first securing mechanism on the second container comprises a thread and wherein the complementary securing mechanism on the connector comprises a complementary thread.

* * * * *